United States Patent [19]

Votel et al.

[11] Patent Number: 5,176,131

[45] Date of Patent: * Jan. 5, 1993

[54] BACK SUPPORT

[75] Inventors: Thomas F. Votel, Sunfish Lake; Susan K. Kulbeik, Blaine, both of Minn.

[73] Assignee: Ergodyne Corporation, St. Paul, Minn.

[*] Notice: The portion of the term of this patent subsequent to Aug. 20, 2008 has been disclaimed.

[21] Appl. No.: 541,604

[22] Filed: Jun. 21, 1990

Related U.S. Application Data

[63] Continuation-in-part of Ser. No. 516,323, Apr. 30, 1990.

[51] Int. Cl.⁵ .............................................. A61F 5/02
[52] U.S. Cl. ..................................... 602/19; 128/845; 128/95.1; 2/305; 2/310
[58] Field of Search ..................... 128/78, 96.1, 101.1, 128/845, 875, 876, 168; 2/305, 310

[56] References Cited

U.S. PATENT DOCUMENTS

| | | | |
|---|---|---|---|
| 1,776,864 | 9/1930 | Cameron | 128/100.1 |
| 2,282,021 | 5/1942 | Benningfield | 128/100.1 |
| 3,101,718 | 8/1963 | Rocker | 2/305 |
| 3,441,027 | 4/1969 | Lehman | |
| 3,521,623 | 7/1970 | Nichols et al. | 128/95.1 X |
| 3,603,316 | 9/1971 | Lehman | 128/546 |
| 3,754,549 | 8/1973 | Nelkin | 128/100.1 |
| 4,545,370 | 10/1985 | Welsh | 128/78 |
| 4,572,167 | 2/1986 | Brunswick | |
| 4,782,535 | 11/1988 | Yewer et al. | |
| 4,836,194 | 6/1989 | Sebastian et al. | 128/78 |

FOREIGN PATENT DOCUMENTS

| | | |
|---|---|---|
| 595742 | 3/1934 | Fed. Rep. of Germany . |
| 2837620 | 8/1978 | Fed. Rep. of Germany . |
| 765416 | 9/1957 | United Kingdom . |

OTHER PUBLICATIONS

European Search Report from Application No. EP 91 10 1967.
Brochure by Comp Equipment Corporation, 1984.

Primary Examiner—Robert A. Hafer
Assistant Examiner—Kerry Owens
Attorney, Agent, or Firm—Merchant, Gould, Smith, Edell, Welter & Schmidt

[57] ABSTRACT

A back support (10) for providing abdominal and lumbosacral support has a waistband (11) of substantially unstretchable construction. An elastic band (30) is operatively connected to the outer surface of the waistband (11). The waistband has a generally V shape, wherein the waistband resists riding up on a wearer. The elastic band is preferably releasably connected to the outer surface of the waistband (11). The support (10) may also have a tool belt (50) operatively connected thereto.

10 Claims, 3 Drawing Sheets

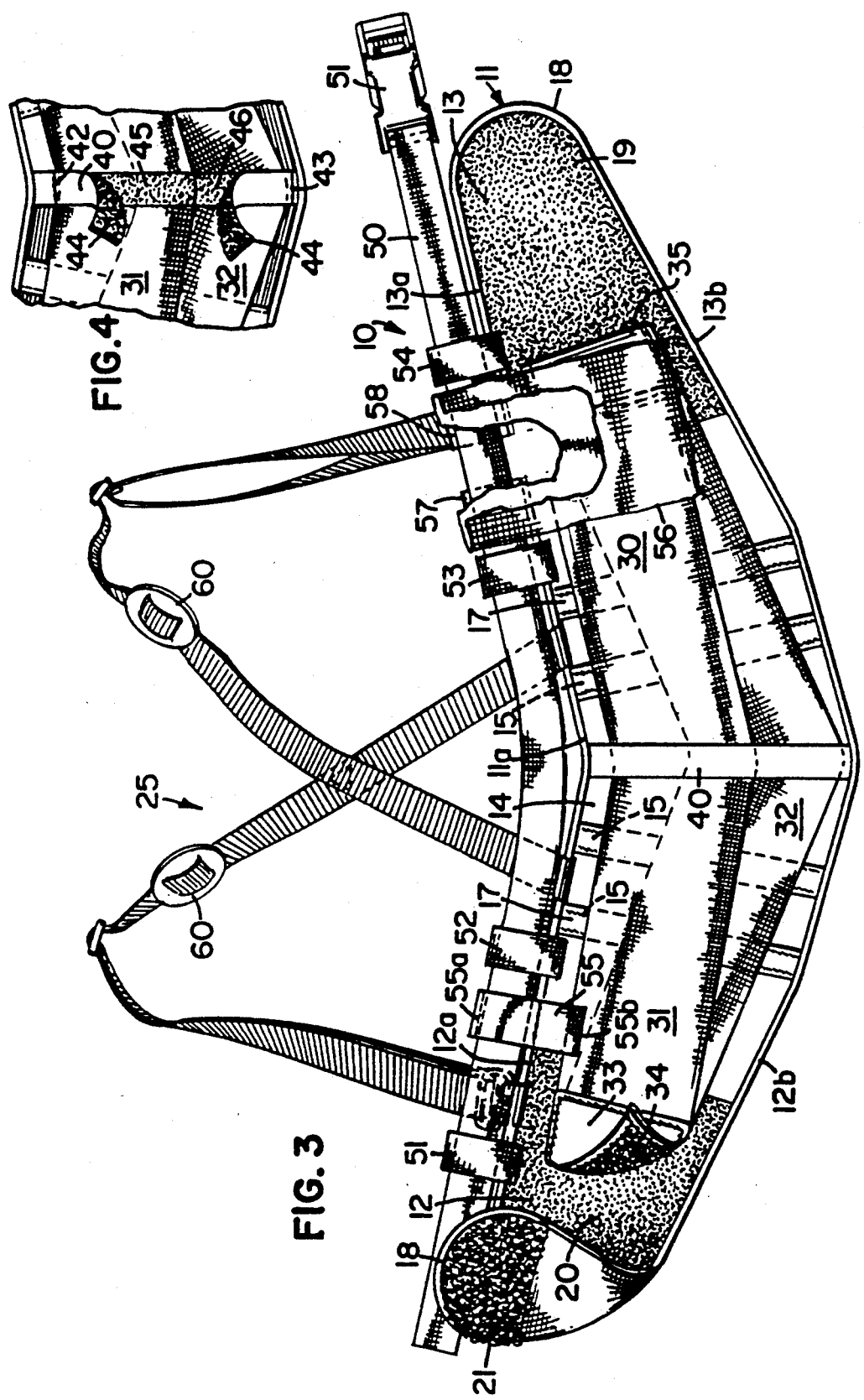

BACK SUPPORT

This application is a continuation-in-part of application Ser. No. 07/516,323, filed Apr. 30, 1990, now pending.

BACKGROUND OF THE INVENTION

1. Field of the Invention

This invention relates generally to back supports and more particularly to a back support designed to prevent riding up of the support and its particularly designed for a female wearer or a wearer whose relationship between the size of the hips and the waist is that generally thought to be representative of a female body.

2. Description of the Prior Art

The present invention is for use by persons who do relatively heavy or awkward lifting, pulling or pushing, and is primarily to help prevent serious back injury by providing abdominal and lumbosacral support. It is not intended to be a therapeutic device for persons who have previous back problems or abdominal muscle injury, although it can be used to help prevent the reoccurrence of such problems. The invention is particularly useful in hospitals or nursing homes by nurses or orderlies or the like who, from time to time, might have to lift or pull up patients or residents and need some support to prevent back problems from occurring, yet during the normal course of their other daily activities, they do not need this aid. They have the need for this type of support device occasionally, so want it handy as the need arises, and also need to be comfortable while wearing the device when not needed for support. Similar applications are to be found for industry use and for workers in other trades and industries. Specifically, the present invention can readily be adapted for use by miners or other workers which need not only the benefit of the prevention of back injury, but also need to carry tools or other items with them. There are a number of stress band type devices which have been used over the years as therapeutic devices for helping to cure various aches and pains due to muscle or other type of damage, and particularly with respect to back problems. Many of these earlier devices are constructed so that they can not be conveniently removed or unfastened and then re-fastened from time to time as the need for the added support comes and goes. In other words, they must be worn full-time or not at all. Still others are bulky and/or cumbersome and/or fairly heavy and if used or worn as an outer garment, interfere with the normal working activities of the users. Other problems with the prior art involve complications in hook up and adjustment, cleaning and not being universal for different sizes and shapes.

For the past several years, the assignee of the present application, Ergodyne Corporation, has sold a back support which has addressed and solved many of the above-noted problems. The support is easy to use, adjustable for many different sizes, easily cleaned, and does not interfere with normal activity. It can readily be temporarily tightened for support when needed and released when normal activities occur.

While the above-mentioned back support has found great popularity and has provided for a much improved product, there are still several areas of concern relating not only to the assignee's back support but others presently available.

When such back supports have been worn by females, the support has tended to ride up on the female during use. While this has not been solely a problem for females, it has been typically been more of a problem for females due to the size of a female's hips in relationship to her waist. Typically, the hips tend to be larger in relationship to their waist. While this is of course not only a characteristic of females, females do tend to have this body shape more often than men. Accordingly, when used throughout this application, reference to females will not be limited to only females, but to persons having the more typical female body shape with respect to the hips in relationship to the waist. Also, depending on the activity engaged in by the wearer, a male may also have his support ride up while in use.

In addition, the elastic band of the back support has typically been secured by means which would not readily release the elastic band. Therefore, when an elastic band was faulty, it was necessary to replace the whole back support. In addition, it has been quite popular to now have a logo or other writing on the elastic band as that is what is visible. When ordered by different companies, they will quite often want their own logo on the elastic band. By previous methods of construction, it was necessary to keep in stock the combination of waistband and elastic band. Applicants have found by having the elastic band removable, the same waistband may be used by many elastic bands having various logos.

Still further, the back supports to date, while comfortable, have tended to be made of a textile material, and have not had efficient transfer of heat and moisture from the wearer of the back support. Still further, for industrial workers using tools, which are normally carried on a tool belt, back supports have not been popular as there have been the necessity of not only wearing a tool belt, but also the back support. This has proved cumbersome and the workers have tended not to wear both. U.S. Pat. No. 4,782,535 does show a belt, typically worn by weight lifters, which has been adapted to hold tools. However, the tools are supported directly from the strap webbing.

The present invention addresses the problems associated with the prior art devices.

SUMMARY OF THE INVENTION

The invention is a back support for providing abdominal and lumbosacral support as needed by the wearer. The back support includes a waistband of a construction having a limited amount of stretch, the waistband having first and second ends and inner and outer surfaces. A means for releasably connecting the first end to the second end is provided so that the waistband may surround the wearer's lower back. An elastic band is operatively connected to the outer surface of the waistband. The elastic band has first and second ends releasably connected to the outer surface of the waistband so as to the be easily moved between an unstretched and stretched position. The waistband has a generally V shape and/or a top circumference less than a bottom circumference, and/or a top circumference which forms a plane generally perpendicular to a torso of a wearer and a bottom circumference which forms a plane which is not perpendicular to the torso of the wearer, wherein the waistband resists riding up on a wearer having the shape of a woman with respect to a relationship of hips to waist.

In a preferred embodiment, the elastic band is releasably connected to the outer surface. The waistband may be made of a fibrous material (all or a portion of) which is designed to transfer heat and moisture away from the body.

In another embodiment, the invention is a back support for providing abdominal and lumbosacral support as needed by the wearer. The back support includes a waistband of substantially unstretchable construction. The waistband has first and second ends and inner and outer surfaces. Further provided is a means for releasably connecting the first end to the second end so that the waistband surrounds a wearer's lower back. An elastic band is operatively connected to the outer surface of the waistband. The elastic band has first and second ends releasably connected to the outer surface so as to be easily moved between an unstretched and a stretched position. A plurality of support loops are provided. The support loops are operatively connected a first end to the waistband, wherein a belt may be supported through the loops.

BRIEF DESCRIPTION OF THE DRAWINGS

FIG. 3 is another front elevational view of a back support shown in FIG. 1 with the additional feature of a tool belt; and FIG. 4 is a view of the loop utilized in the back support in FIG. 1 for releasably holding the elastic band.

DETAILED DESCRIPTION OF THE PREFERRED EMBODIMENT

Figure 1:
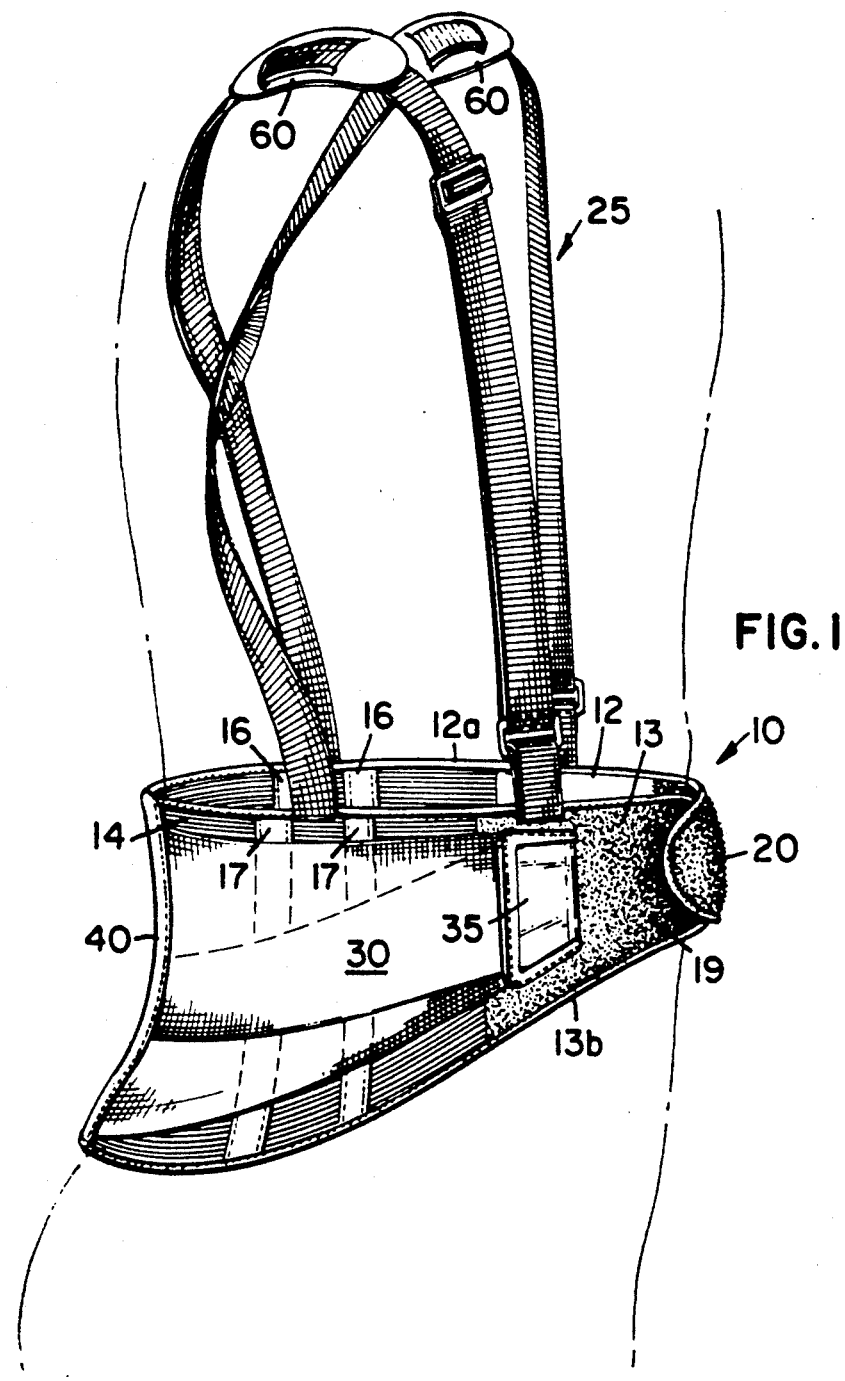
FIG. 1 is a perspective view of the back support of the present invention.

As shown in the drawings, wherein like numerals represent like parts throughout the several views, there is generally disclosed at 10 a back support. The back support 10 includes a waistband 11 having a left half 12 and a right half 13. While this is referred to as a waistband, it is understood that the waistband 11 is designed to rest below the navel and accordingly is not defined as being literally a band around the waist, but also may be below the waist. A piece of fabric 14, is cut to the size of the entire waistband 11. Depending upon the embodiment of the invention to be constructed, the fabric 14 may be made of either a stretchable or unstretchable fabric. As will be discussed more fully hereafter, in one embodiment it is desired to have some stretchability to the waistband 11, while in other embodiments, such as when a tool belt is hung from the back support, it is desirable to not have any stretch to the waistband 11. If a stretchable materials desired, a suitable material, such as spandex, may be utilized. If it is desired to have a non-stretchable fabric, any suitable material, such as apex, may be utilized. A plurality of semi-rigid stays 15 are secured to the waistband 11. On the inside of the waistband 11, the stays 15 are covered by a rubberized elastic fabric 16 and on the outside by a vinyl fabric 17. As shown in the Figures, two stays 15 are utilized on both the left half 12 and right half 13. A ribbing or binding 18 is stitched around the periphery of the entire waistband 11. A loop fabric 19 is stitched to the outside of the right half 13 and a loop fabric 20 is stitched to the outside of the left half 12. On the inside of the left half 12 of the waistband 11, a hook material 21 is secured by stitching. The hook material 21 and loop fabric 19 and 20 may be of any type well-known in the industry which would form a hook and loop type fastener such as Velcro brand. The fabric 14 may be somewhat stretchable, however, the fabrics 19 and 20 are substantially non-stretchable. The fabric 14 may be suitable material such as the made stretchable Spandex ® material. The binding 18 may be made of a suitable material such as tricot. As previously stated, if a stretchable material such as spandex is utilized, the overall waistband will have some stretchability. For instance, with a waistband 11 having an overall length of approximately 42 inches, the waistband 11 may expand from ½ to 3 inches and preferably from 1 ½ to 2 inches. This allows the waistband 11 to have the capabilities of stretching and conforming to the body of the wearer. The waistband 11 has a top edge 12a and 13a and a bottom edge 12b and 13b. As can be seen in the drawings, the right half 12 and the left half 13 form a generally V-shaped waistband 11. As shown in the drawings, each half 12 and 13 form an angle of approximately 13° with a horizontal line. It has been found preferably to have this angle to be between 4°–35°, preferably 5°–20° and still further to be preferred 8°–18°. At less than 4°, there is no benefit for preventing the support from riding up. At greater than 35°, it is difficult to fit or wear the support. The waistband would end up too far above the waistline in front. At 4°, the waistband right and left half form an angle of 172°, and at 35° they form an angle of 110°. When referring to the angle formed by the two halves, the preferable range is therefore 110°–172°, preferably 140–170° and still further to be preferred 144°–164°. Adjustable suspenders, generally designated as 25, are secured to the top edge 12a and 13a of the waistband 11. The suspenders 25 may be of any type well known in the art and have shoulder pads 60. Also, the suspenders may be detachable. In another embodiment the waistband 11 may have a fibrous material laminated thereto to allow heat and moisture to be transferred away from the body of the wearer. Such a suitable fabric may be a Coolmax ™ fabric by DuPont. The fabric is simply laminated to the waistband 11 such that the fabric is adjacent the wearer of the body. Alternately, instead of being laminated to the waistband 11, the fabric (Coolmax) may be used in place of the Spandex ® material forming the waistband 11.

Figure 2:
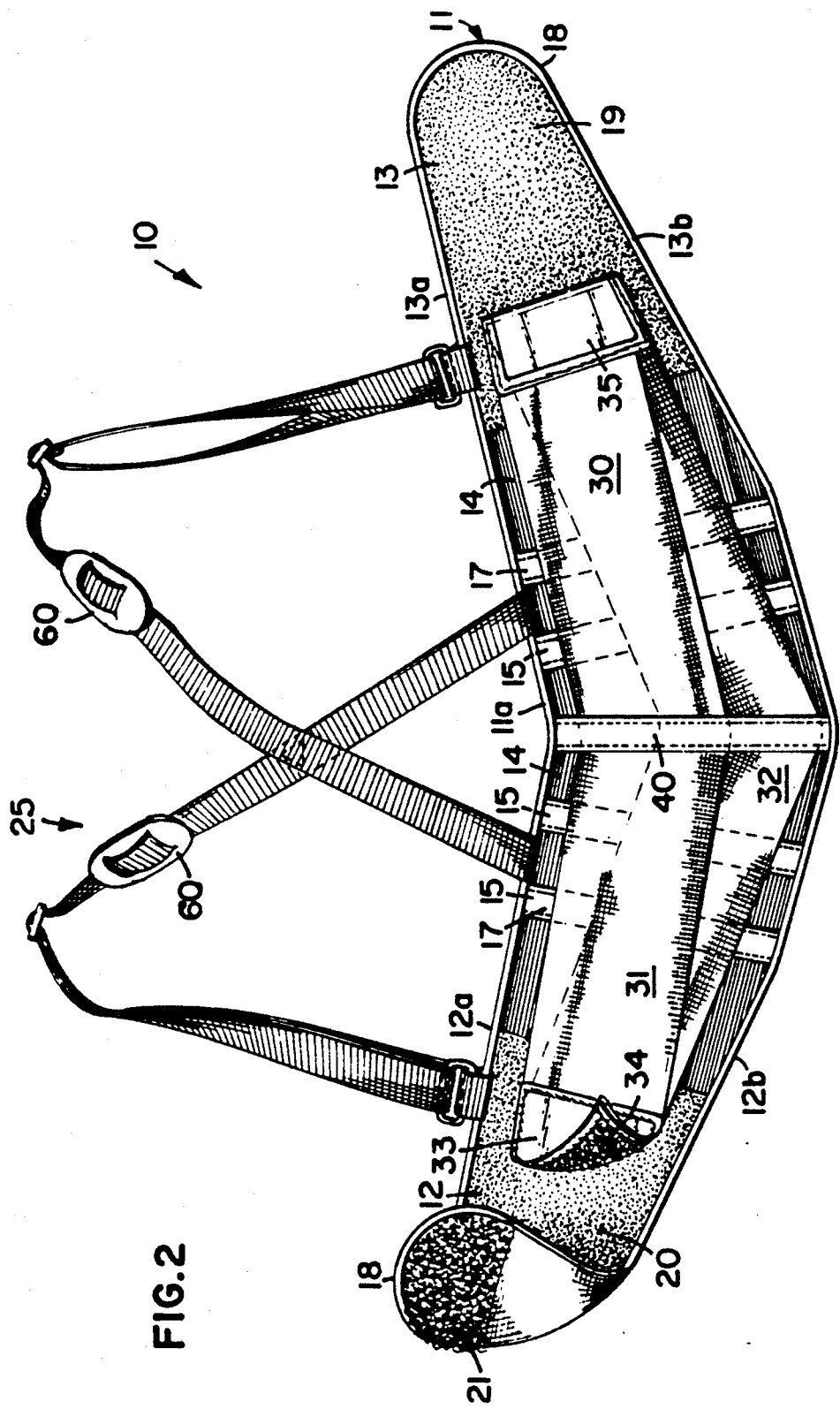
FIG. 2 is a front elevational view of the back support shown in FIG. 1, with the back support being in an unfolded layout.

A four inch wide elastic band, designated generally as 30, has a top four inch band 31 and a bottom four inch band 32. The top band 31 is generally rectangular but has a slight V-shape and the bottom band 32 has more of a V-shape. The bands 31 and 32 are connected to each other at their ends and at the left end of bands 31 and 32 are connected by a vinyl piece 33 on the outside surface and a hook material 34 on the bottom surface. Similarly, the right ends are connected and has a vinyl piece 35 and a hook material underneath (not shown). The vinyl pieces 33 and 35 may also be any suitable material which is easily cleaned and is durable such as rubber or polyurethane. A loop 40 has a first end operatively connected, such as by stitching 42, proximate the top surfaces 12a and 13a and a second end operatively connected, such as by stitching 43, proximate the bottom edges 12b and 13b. This loop 40 is shown in more detail in FIG. 4. The top stitching 42 and bottom stitching 43 only fastens the ends of the loop 40 to the waistband 11. Accordingly, there is an opening between the waistband and the underneath side of the loop through which the elastic band 30 may be positioned. The loop 40, as shown in FIG. 4 is for illustrative purposes, and the loop 40 is actually continuous as shown in FIGS. 1, 2 and 3. The loop in FIG. 4 is broken and bent back to illustrate the hook material 44 that is on the other side of the loop 40. Cooperatively connected to the outside surface of the first band 31 is a loop material 45 and cooperatively connected to the outside of the second band 32 is a loop material 46. The hook material 44 and loop material 45 and 46 form a two part fastener, and any suitable fastener, such as a Velcro brand may be used. Each of the bands 31 and 32 may be of any suitable length, such as approximately 24 inches when not stretched. When stretched, this length may be increased to a suitable length so as to provide the necessary support. While the specific design of the support will dictate the length of the stretch desired, it has been found that from 5 to 15 inches and preferably from about 9 to 13 inches and still more preferably 10 to 12 inches of stretch is desirable.

A belt 50, having a buckle 51 operatively connected thereto, is attached to the waistband 11. Four straps 51, 52, 53 and 54 have their first ends operatively connected, such as by stitching, to the waistband 11. Their second ends have a loop through which belt 50 may pass and be supported thereby. On the belt 50 may be hung a variety of carriers or attachments. For instance, a simple strap 55 may have a first loop 55a through which the belt 50 may be passed and a second loop 55b through which a tool may be hung. Similarly, a pouch 56 may have two straps 57 and 58 attached thereto. The straps 57 and 58 have a loop through which the belt 50 may be passed. The pouch 56 may then be utilized to place various piece of equipment or items to be used by the wearer. The belt 50 may be specifically designed for the support 10, or may be any belt, such as a miner's belt, which may have a variety of well-known constructions.

In operation, the wearer places the suspenders 25 over her shoulders so that the right side 13 is on her right side and the left side 12 is on her left side. Then, the tension of the elastic band 30 is released by removing the ends of the elastic band away from the fabric 20 and 19. The elastic band 30, at this point, is held in position only by the loop 40 with the ends of the elastic band 30 hanging free. Then, the wearer grasps each end of the waistband 11 and stretches the right end 13 across the left and places the hook material 18 on top of the fabric 19 to secure the waistband in position. It is important that the waistband 18 firmly supports the lower back/upper buttocks. The upper edge of the waistband 12a and 13a should be below the navel.

The wearer then continues to wear the back support with the elastic band 30 having its end either loose or attached to the fabrics 19 and 20 in an unstretched state. Then, just before lifting, the ends are grabbed at locations 33 and 35 and stretched as far forward as possible, and then placed against the fabric 19 and 20 so that the hook material 34 on the left side and the hook material on the comparable right side fastens the elastic band in a stretched position.

FIG. 1 shows the device 10 on a wearer. As previously mentioned, the design of the present support 20 prevents the riding up of the support 10 during use. Because of the V-shaped waistband, the two halves 12 and 13 are able to move around the larger pelvis area without causing the support 10 to ride up as the wearer continues to wear the support 10. The prior art devices tended to have the waistband 11 generally rectangular so that, when put over the larger hips of a wearer, the prior art devices tended to ride up on the wearer.

The back support 10 has a top circumference, measured about 12a and 13a which is less than the bottom circumference measured about 12b and 13b. This is due to the V-shaped configuration of the waistband. It is contemplated that other configurations may be utilized which would have a smaller top circumference and a bottom circumference, thereby preventing the waistband from riding up on the wearer.

As shown in FIG. 1, the top circumference forms a plane which would be generally perpendicular to the torso of the wearer. In contrast, the bottom surface 12a and 12b generally forms a plane which is not perpendicular to the torso. If the waistband 11 would be of even width throughout, the bottom plane would tend to be closer to perpendicular to the torso of the wearer.

If the elastic band 30 is worn out or damaged, it can easily be replaced. The ends of the elastic band simply are removed from the velcro type fastener and one end is slipped out through the opening in the loop 40. It is then an easy matter to simply insert a new elastic band 30. This also is quite advantageous in keeping inventories low. If a logo of a business, such as a hospital, wishes to be on the elastic band, it is only necessary to inventory the elastic bands and not the combination of waistband and elastic bands. Therefore, numerous elastic bands with different logos can be in inventory without the necessity of having a large inventory of completed supports including waistbands.

The belt 50 support by straps 51-54 allows the wearer to wear a single support and also have a tool belt or miner's belt attached thereto. It is not necessary to have two separate devices around the wearer. In addition, the belt 50 with the item holders may also be utilized on a standard back support 10 that does not have the general V-shape.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as presented herein. All alternative modifications and variations of the present invention which follow in the spirit and broad scope of the appended claims are included.

I claim:

1. A back support for providing abdominal and lumbosacral support as needed by the wearer, comprising:
    (a) a waistband of a construction having a limited amount of stretch, said waistband having first and second ends and inner and outer surfaces;
    (b) means for releasably connecting said first end to said second end so that said waistband surrounds a wearer's lower back;
    (c) an elastic band operatively connected to said outer surface of said waistband, said elastic band having first and second ends releasably connected to said outer surface, so as to be easily moved between an unstretched and a stretched position;
    (d) said waistband having generally V shape, wherein the waistband forms an angle of from 110° to 172°, wherein said waistband resists riding up on a wearer.

2. The support of claim 1, wherein the waistband forms an angle of from 140°-170°.

3. The support of claim 1, wherein the waistband forms an angle of from 144°-164°.

4. The back support of claim 1, wherein said elastic band is releasably connected to said outer surface.

5. The back support of claim 4, further comprising a loop having a first end connected to a top edge of said outer surface and a second end connected to a bottom edge of said outer surface, thereby forming an opening through which said elastic band is positioned.

6. The back support of claim 5, further comprising a strip of one part of a two part hook and a loop fastener attached to said loop and the other part of the two part fastener attached to said elastic band so as to engage said strip when said elastic band is positioned in said loop.

7. The back support of claim 1, wherein said waistband is made of a fibrous material designed to transfer heat and moisture away from the body.

8. The back support of claim 1, further comprising reinforcement pads operatively connected to each of said first and second ends of said elastic band.

9. The back support of claim 1, further comprising means for suspending said back support from shoulders of the wearer.

10. The back support of claim 1, further comprising:
(a) a plurality of support loops, said support loops operatively connected at a first end to said waistband;
(b) a belt supported through said support loops; and
(c) means for attaching items to said belt.

* * * * *